US00PP20943P3

(12) United States Plant Patent
Layt

(10) Patent No.: US PP20,943 P3
(45) Date of Patent: Apr. 27, 2010

(54) ***PHORMIUM TENAX* PLANT NAMED 'PHOS3'**
(50) Latin Name: *Phormium tenax*
Varietal Denomination: PHOS3

(76) Inventor: Todd Anthony Layt, P.O. Box 1011, Richmond, NSW (AU) 2753

( * ) Notice: Subject to any disclaimer, the term of this patent is extended or adjusted under 35 U.S.C. 154(b) by 0 days.

(21) Appl. No.: 11/999,870

(22) Filed: Dec. 7, 2007

(65) Prior Publication Data

US 2008/0141410 P1 Jun. 12, 2008

Related U.S. Application Data

(60) Provisional application No. 60/873,450, filed on Dec. 7, 2006.

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent L Bell

(57) ABSTRACT

'PHOS3' is a distinctive variety of *Phormium tenax* which is characterized by the combination of its medium upright growth habit, orange tones incorporated into its bronze leaf color, narrower leaf width and resistance to phytophthora root rot.

3 Drawing Sheets

Latin name of the genus and species: The Latin name of the genus and species of the novel variety disclosed herein is *Phormium tenax.*

Variety denomination: The inventive variety of *Phormium* disclosed herein has been given the variety denomination 'PHOS3'.

BACKGROUND OF THE INVENTION

The present invention relates to a new and distinct perennial variety of *Phormium tenax*, which has been given the variety denomination of 'PHOS3'. Its market class is that of an ornamental plant. 'PHOS3' is intended for use in landscaping and as a decorative plant.

The *Phormium tenax* variety 'PHOS3' was finally selected in 2002 in an Australian nursery in the state of New South Wales following a selection process carried out from 1999 to 2001 involving large quantities of common open pollinated *Phormium tenax* production stock. 'PHOS3' is a single seedling selected from open pollinated common *Phormium tenax*. 'PHOS3' was selected due to its bronze with orange toned leaf color and survival from exposure to the plant pathogen phytophthora, known as phytophthora root rot. 'PHOS3' was first propagated asexually by division in the state of New South Wales, Australia and has since been asexually propagated by division and micropropagation. The distinctive characteristics of the inventive 'PHOS3' variety are stable from generation to generation; clones of the variety produced by asexual reproduction maintain the distinguishing characteristics of the original plant. In comparing 'PHOS3' to "common *Phormium tenax*" reference to "common" means typical seedling forms of un-improved or wild types as used in hoticultural industries and home gardens.

'PHOS3' has a medium growth habit with a medium shoot density whereas common *Phormium tenax* has a variable growth form ranging from short to tall plant height and sparse to dense shoot density. 'PHOS3' has orange tones incorporated into its bronze leaf color whereas other bronze colored *Phormium tenax* do not have such orange tones prominent. 'PHOS3' has a narrow leaf width compared to other forms of

*Phormium tenax*. 'PHOS3' has a strong resistance to phytophthora root rot whereas common *Phormium tenax* has weak resistance.

An application for plant breeders' rights for variety 'PHOS3' has been lodged with the Australian Plant Breeders' Rights Office, and was first gazetted in January 2006 under Application No. 2005/350.

SUMMARY OF THE INVENTION

'PHOS3' is a distinctive variety of *Phormium tenax* which is characterized by the combination of its medium upright growth habit, orange tones incorporated into its bronze leaf color, narrow leaf width and resistance to phytophthora root rot.

BOTANICAL DESCRIPTION OF THE PLANT

The following is a detailed botanical description of a new and distinct variety of a *Phormium tenax* ornamental plant known as 'PHOS3'. Plant observations were made on plants grown in New South Wales, Australia. Unless indicated otherwise, the descriptions disclosed herein are based upon observations made in July 2005 of 26 week old 'PHOS3' plants grown in nursery pots and field plots.

Those skilled in the art will appreciate that certain characteristics will vary with older or, conversely, younger plants. 'PHOS3' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition. It is useful to note that many of the grayed orange colors quoted in the RHS charts describe what are commonly referred to as brown colors.

'PHOS3' is a perennial *Phormium tenax* plant which is a seedling selection from a common *Phormium tenax* purple form. After its selection, 'PHOS3' was asexually propagated by division and then by micropropagation. 'PHOS3' has a bronze leaf color with orange tones.

These features and other characteristics are apparent from the description provided below.

Figure 1:
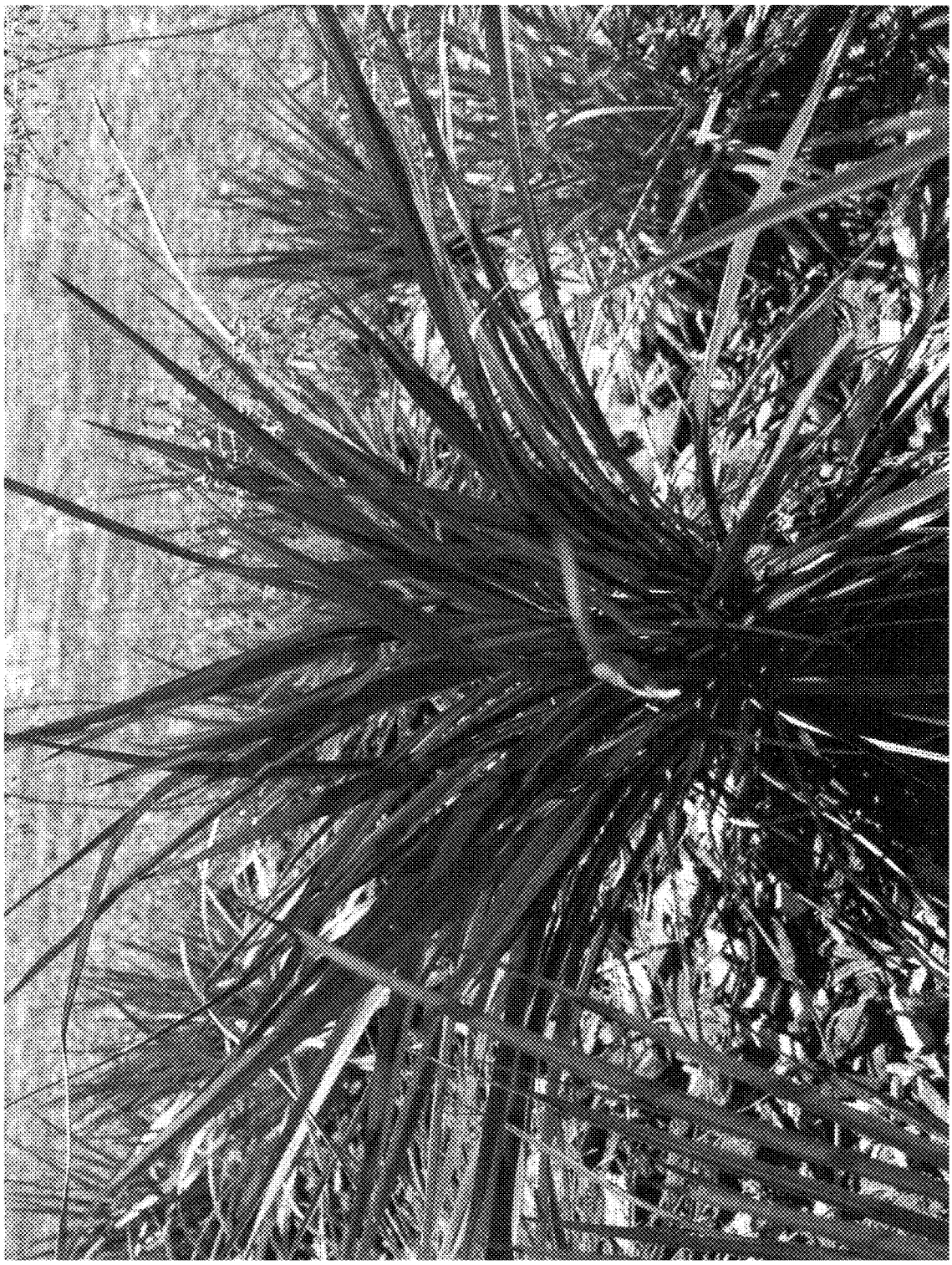
FIG. 1 shows a 'PHOS3' plant.
Figure 2:
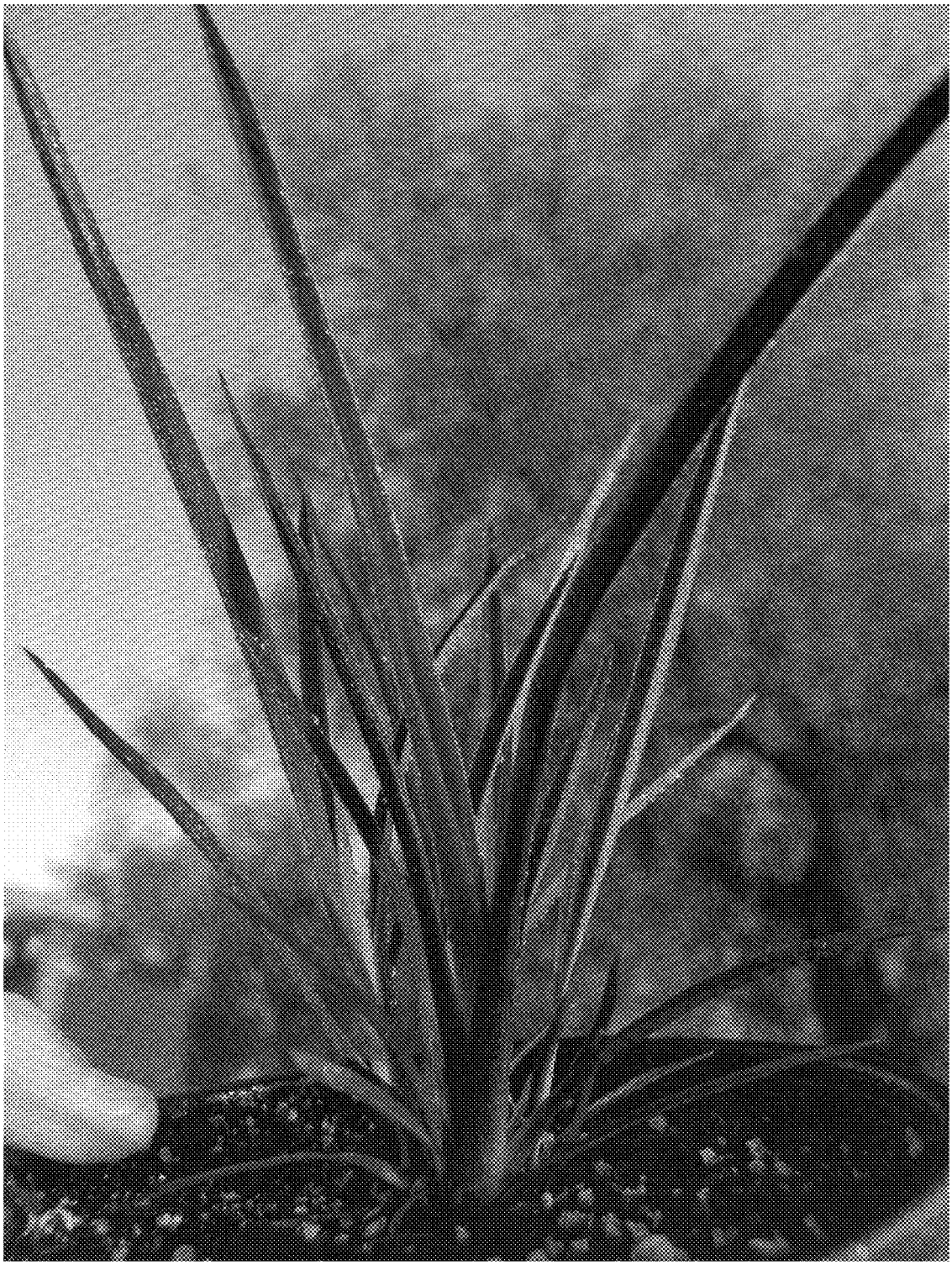
FIG. 2 shows a 'PHOS3' plant showing green color at shoot base.
Figure 3:
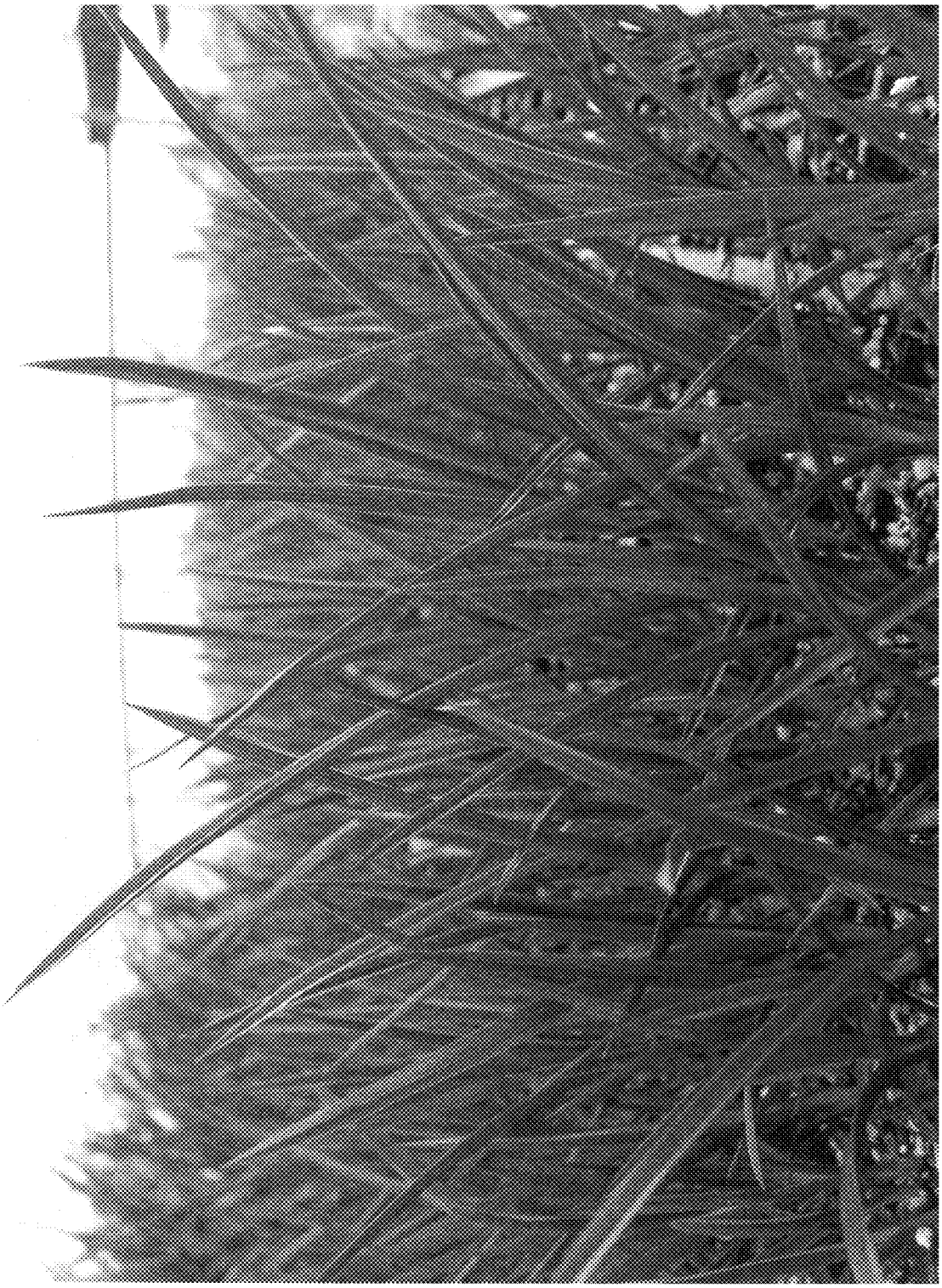
FIG. 3 shows 'PHOS3' plants displaying orange tone of foliage.

Growth habit, dimensions and color: 'PHOS3' is a medium, rhizomatous plant forming an upright fan shaped tuft. Average plant height is to 60 cm and average plant spread is 60 cm in a mature plant grown in a garden in Sydney, New South Wales, Australia (observed spring 2006). A representative 'PHOS3' plant is shown in FIG. 1. The upper side of the mature leaf is grayed orange in color (observed summer 2005) corresponding to approximately RHS 177A. The mature leaf also exhibits many orange tones corresponding to grayed oranges RHS 172A, RHS 173A and RHS 173B. Occasionally it also exhibits redder tones corresponding to grayed red RHS 180A. Leaf margins and mid ribs do not contrast prominently with the leaf blade. The leaf lower side color corresponds to the upper leaf side. Immature leaves occasionally exhibit grayed purple coloration corresponding to RHS 183A. Overall foliage coloration is highlighted by orange tones (see FIG. 3). The leaf is generally 20–30 mm in width, and reaches an average length of 45–52 cm. The leaf shape is linear-ensiform, leaf base is cauline (petioles absent), leaf margin is entire, leaf apex is acute and leaf surface texture is characterised by fine striations. The leaf venation pattern is parallel; the color is the same as the rest of the leaf. The leaf attitude is erect. The color of the base of the shoot where the leaves unite is yellow green (RHS144B) (see FIG. 2).

Roots: The roots of 'PHOS3' are fleshy and thick, similar to other *Phormium tenax*.

Inflorescence: Flower development has not been observed on the new variety. Still has not flowered.

Flowers: Flower development has not been observed on the new variety. Still has not flowered.

Comparison of PHOS3 with other varieties of *Phormium tenax: 'PHOS*3' has a medium sized upright growth habit with a narrower leaf width and orange tones incorporated into its bronze leaf color combined with stronger resistance to phytophthora root rot than common *Phormium tenax* known to the inventor.

'PHOS3' has a more orange colored overall foliage appearance than common *Phormium tenax* known to the inventor and another comparable type known as 'Bronze Baby' (unpatented) whereas common *Phormium tenax* is highly variable from grayed green to grayed purples and 'Bronze Baby' has an upper side leaf color grayed orange (approximately RHS 177A) with no obvious orange or red tones. 'Bronze Baby' looks brown in overall foliar appearance whereas 'PHOS3' has a more orange overall foliar appearance. 'PHOS3' has a narrower leaf width than common *Phormium tenax* known to the inventor or 'Bronze Baby' (statistical data collection in progress). 'PHOS3' has also demonstrated a stronger resistance to the disease phytophthora root rot in nursery pots in Sydney, New South Wales, Australia than common *Phormium tenax* known to the inventor.

'PHOS3' differs from the variety 'PHORD1' (U.S. Plant Pat. No. 18,865) as it has a more orange colored overall foliage appearance whereas 'PHORD1' has a more reddish foliage color.

The combination of its medium upright growth habit, orange tones incorporated into its bronze leaf color, narrow leaf width and resistance to phytophthora root rot makes 'PHOS3' a desirable ornamental plant suited for mass production for pot and landscape use.

Flower development has not been observed on 'PHOS3'. The novelty and distinctiveness of 'PHOS3' as compared with other varieties of *Phormium tenax* is currently being further collated by vegetative measurements in field trials in Sydney, Australia.

Asexual reproduction: After its initial discovery, 'PHOS3' was transplanted into a 140 mm pot for further trials and testing. After divisions were made for several subsequent generations, 'PHOS3' was observed to retain color and size characteristics that were noted in the original 'PHOS3' seedling. Divisions of 'PHOS3' root within 3 to 4 weeks. 'PHOS3' was divided into several pots for further evaluation. Potting mix used contained 50% sand and 50% peat. Plants were divided into 90 mm×50 mm×50 mm tubes. 'PHOS3' has been propagated in vitro using micropropagation and has been observed to reproduce from generation to generation in a uniform and stable manner maintaining original color and size characteristics.

Environmental tolerances: 'PHOS3' has typical shade tolerance for the species. The winter hardiness of 'PHOS3' is at least to zone 8a–8b in the Southeastern United States, and evaluation of winter hardiness is ongoing. 'PHOS3' has been observed to hold color to −8 degrees Celsius without any noticeable change in appearance of the plant. 'PHOS3' has moderate to good drought tolerance. 'PHOS3' has moderate to good recovery with watering after severe wilting. 'PHOS3' does well in sandy soils, but also tolerates heavy, clay-type soils well. 'PHOS3' has been observed to be hardier in high humidity conditions than common *Phormium tenax*.

Pest and disease resistance: 'PHOS3' has excellent resistance to root rot compared to other similar *Phormium tenax* cultivars known to the inventor. 'PHOS3' has average resistance to pests similar to other *Phormium tenax* cultivars.

That which is claimed is:

1. A new and distinct variety of *Phormium tenax* plant named 'PHOS3', substantially as described and illustrated herein.

* * * * *